US012740955B2

(12) United States Patent
Murphy et al.

(10) Patent No.: US 12,740,955 B2
(45) Date of Patent: Sep. 22, 2026

(54) TREATMENT OR PREVENTION OF ISCHAEMIC STROKE REPERFUSION INJURY

(71) Applicant: Cambridge Enterprise Limited, Cambridge (GB)

(72) Inventors: Michael Patrick Murphy, Cambridge (GB); Thomas Krieg, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 1141 days.

(21) Appl. No.: 17/781,297

(22) PCT Filed: Dec. 8, 2020

(86) PCT No.: PCT/GB2020/053141
§ 371 (c)(1),
(2) Date: May 31, 2022

(87) PCT Pub. No.: WO2021/116670
PCT Pub. Date: Jun. 17, 2021

(65) Prior Publication Data

US 2022/0409562 A1 Dec. 29, 2022

(30) Foreign Application Priority Data

Dec. 9, 2019 (GB) .................................... 1918022

(51) Int. Cl.

| | |
|---|---|
| ***A61K 31/194*** | (2006.01) |
| ***A61K 45/06*** | (2006.01) |
| ***A61P 9/10*** | (2006.01) |

(52) U.S. Cl.
CPC ............ *A61K 31/194* (2013.01); *A61K 45/06* (2013.01); *A61P 9/10* (2018.01)

(58) Field of Classification Search
CPC .... A61K 31/194; A61K 31/22; A61K 31/225; A61P 9/10
See application file for complete search history.

(56) References Cited

U.S. PATENT DOCUMENTS

| | | | | |
|---|---|---|---|---|
| 10,603,298 | B2 * | 3/2020 | Chouchani .............. | A61P 35/00 |
| 2024/0252457 | A1 * | 8/2024 | Krieg ........................ | A61P 9/10 |

FOREIGN PATENT DOCUMENTS

| | | |
|---|---|---|
| CN | 109966278 | 7/2019 |
| WO | WO 2016/001686 | 1/2016 |
| WO | WO 2017/142855 | 8/2017 |
| WO | WO 2017/192413 | 11/2017 |

OTHER PUBLICATIONS

Davidson et al., (2019) "Multitarget Strategies to Reduce Myocardial Ischemia/Reperfusion Injury", Journal of the American College of Cardiology, 73:89-99.
Feigin et al., (2014) "Global and Regional Burden of Stroke during 1990-2010: Findings from the Global Burden of Disease Study 2010", Lancet, 383(9913):245-254.
Francisco Campos et al., (2011) "Neuroprotection by Glutamate Oxaloacetate Transaminase in Ischemic Stroke: An Experimental Study", Journal of Cerebral Blood Flow & Metabolism, vol. 31, No. 6, pp. 1378-1386.
International Preliminary Report on Patentability for PCT Application No. PCT/GB2020/053141., May 17, 2022 7 pages.
Kalogeris et al., (2012) "Cell Biology of Ischemia/Reperfusion Injury", International Review of Cell and Molecular Biology, 298:229-317.
Kloner et al., (2017) "New and Revisited Approaches to Preserving the Reperfused Myocardium", Nature Reviews Cardiology, 14:679-693.
Kula-Alwar et al., (2019) "Targeting Succinate Metabolism in Ischemia/Reperfusion Injury", Circulation: 140, 1968-1970.
Martin et al., (2019) "Succinate Accumulation Drives Ischemia-Reperfusion Injury during Organ Transplantation", Nature Metabolism, 1:966-974.
Murphy & Steenbergen (2008) "Mechanisms Underlying Acute Protection from Cardiac Ischemia-Reperfusion Injury", Physiological Reviews, 88:581-609.
Prag et al., (2022) "Ester Prodrugs of Malonate with Enhanced Intracellular Delivery Protect Against Cardiac Ischemia-Reperfusion Injury In Vivo", Cardiovasc Drugs Therapy, 36:1-13.
Prag et al., (2022) "Ischemia-Selective Cardioprotection by Malonate for Ischemia/Reperfusion Injury", Circ Res. 131(6):528-541.
Silachev et al., (2015) "Magnetic Resonance Spectroscopy of the Ischemic Brain under Lithium Treatment. Link to Mitochondrial Disorders under Stroke", Chemico-Biological Interactions, vol. 237, pp. 175-182.
Tang et al., (2013) "The Cardioprotective Effects of Citric Acid and L-Malic Acid on Myocardial Ischemia/Reperfusion Injury", Evidence-Based Complementary and Alternative Medicine, vol. 2013, Article ID 820695, 11 pages.
Valls-Lacalle et al., (2015) "Succinate Dehydrogenase Inhibition with Malonate during Reperfusion Reduces Infarct Size by Preventing Mitochondrial Permeability Transition", Cardiovascular Research, vol. 109, No. 3, pp. 374-384.
Valls-Lacalle et al., (2018) "Selective Inhibition of Succinate Dehydrogenase in Reperfused Myocardium with Intracoronary Malonate Reduces Infarct Size", Scientific Reports, vol. 8, No. 1, 10 pages.
Yin et al., (2021) "Structural Basis for a Complex I Mutation that Blocks Pathological ROS Production", Nat Commun 12 pages.

* cited by examiner

*Primary Examiner* — Irina Neagu
(74) *Attorney, Agent, or Firm* — Rudy J. Ng; Bozicevic, Field & Francis LLP

(57) ABSTRACT

The present invention relates to salts and compositions for use in the treatment of ischaemic stroke reperfusion (IR) injury. In particular, the present invention relates to a salt of formula (I) for use in treating or preventing ischaemic stroke reperfusion injury, wherein X, Y, n, m, Z, A and B are as defined herein.

19 Claims, 9 Drawing Sheets

TREATMENT OR PREVENTION OF ISCHAEMIC STROKE REPERFUSION INJURY

FIELD

The present invention relates to salts for use used in the treatment or prevention of ischaemic stroke reperfusion (IR) injury.

BACKGROUND TO THE INVENTION

Stroke is a major health problem worldwide. Recent estimations (Feigin V L et al. *Global and regional burden of stroke during* 1990-2010*: findings from the Global Burden of Disease Study* 2010. *Lancet.* 2014; 383(9913):245-254) indicate that the global prevalence rate is 5 strokes per 1000 person-years, corresponding to 33 million people living after a stroke. 5.9 million people suffered a stroke-related death in 2010, and stroke resulted in more than 102 million lost disability-adjusted life years (DALYs), corresponding to the sum of premature death and years of healthy life lost attributed to disability.

In recent decades, little progress has been made in stroke therapy options and, correspondingly, little progress has been made in reducing mortality/morbidity rates.

Currently, there is no specific therapy for ischaemic stroke other than stopping the ischaemic insult via thrombectomy or thrombolysis. Minimising the ischaemic time is key to salvaging ischaemic tissue.

However, any therapy interfering with clotting cannot be used for emergency treatment of ischaemic stroke, because such therapies are detrimental in the case of haemorrhagic stroke.

Thus, patients suspected of suffering an ischaemic stroke must first be imaged, for example using MRI or CT imaging, to determine the type of stroke before effective drugs for the treatment of stroke, such as clopidogrel/ticagrelor or aspirin, or other clot-dissolving drugs, can be administered.

Thus, valuable time is lost due to the need for emergency imaging, elongating the ischaemic time.

Once the ischaemic insult is stopped, the reperfusion of blood into ischaemic tissue is itself damaging, resulting in stroke ischaemia/reperfusion (IR) injury.

There is a clear unmet clinical need for drugs which reduce the extent of IR injury following stroke.

SUMMARY OF THE INVENTION

In view of the above, there remains a need to develop compounds and compositions for use in the treatment and prevention of ischaemic stroke reperfusion injury which are not detrimental to the patient in the case of haemorrhagic stroke. Such compounds and compositions could be administered as an emergency stroke medication (i.e. before diagnosis of the type of stroke), thus improving clinical outcomes for ischaemic stroke patients by reducing the damage caused upon reperfusion once the ischaemic insult is halted.

There is also a need in general for improved compounds and compositions useful for the treatment or prevention of ischaemic stroke reperfusion injury. Ideally, such improved compounds and compositions could be administered prior to removing the ischaemic event to reduce the injury caused when reperfusion commences. Ideally, such compounds and compositions could also be administered in conjunction with therapies intended to chemically or mechanically remove an ischaemic event, e.g. a blood clot.

The present invention relates to a salt of formula (I):

Formula (I)

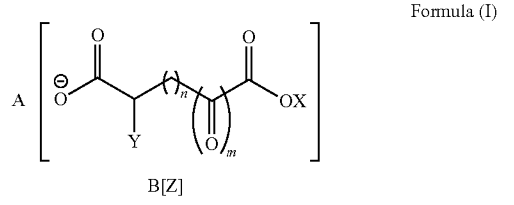

for use in treating or preventing ischaemic stroke reperfusion injury;

wherein X is selected from a negative charge, H, or $C_1$-$C_{12}$ alkyl;

wherein Y is selected from H, OH or $C_1$-$C_{12}$ alkyl;

wherein n is 0 or 1;

wherein m is 0 or 1;

wherein Z is one or more pharmaceutically acceptable cations; and wherein A and B are independently any integer, such that the net charge of the salt is 0.

The present invention also relates to said salt of formula (I) for use as an emergency medication following suspected stroke, before diagnosis of the type of stroke.

The present invention also relates to a composition for use in treating or preventing ischaemic stroke reperfusion injury comprising the salt of formula (I) in combination with one or more pharmaceutically acceptable excipients, carriers or diluents.

Preferably, the above salt of formula (I) is a salt of formula (II) as defined below, more preferably a malonate salt.

DETAILED DESCRIPTION OF THE INVENTION

Following ischaemic stroke, timely reperfusion is critical for salvaging the ischaemic tissue. Paradoxically, however, reperfusion of blood into the ischaemic tissue is damaging in itself, leading to stroke ischaemia/reperfusion (IR) injury.

Current best clinical practice is to conduct rapid reperfusion to minimise the ischaemic time. However, this may result in extensive IR injury, and there is a clear unmet clinical need for drugs which reduce the extent of IR injury following stroke.

Historically, IR injury was thought of as a random and chaotic series of damaging events resulting in the formation of reactive oxygen species (ROS) from reperfusion ischaemic tissue.

It has recently been shown that metabolic mechanisms within mitochondria are central to IR injury. The citric acid cycle metabolite succinate has been accumulate in tissue during ischaemia. During reperfusion, this succinate is rapidly oxidised by succinate dehydrogenase (SDH), driving a spike in ROS production by the mitochondrial complex I[2]. This ROS pulse, together with calcium dysregulation and ATP depletion, initiates a cascade of damaging events culminating in reperfusion injury. This reperfusion leads to damage over and above that of the ischaemia alone. Developing drugs that reduce reperfusion injury following ischaemic stroke thus provides a therapeutic window to reduce organ damage.

SDH is a key enzyme in succinate formation during ischemia and its oxidation upon reperfusion. It is thought that ischaemic stroke reperfusion injury may be ameliorated by altering succinate metabolism, either by preventing its accumulation during ischemia (thus less succinate is available to be oxidised during reperfusion) or directly blocking its oxidation during reperfusion (e.g. by inhibiting SDH).

Figure 3:
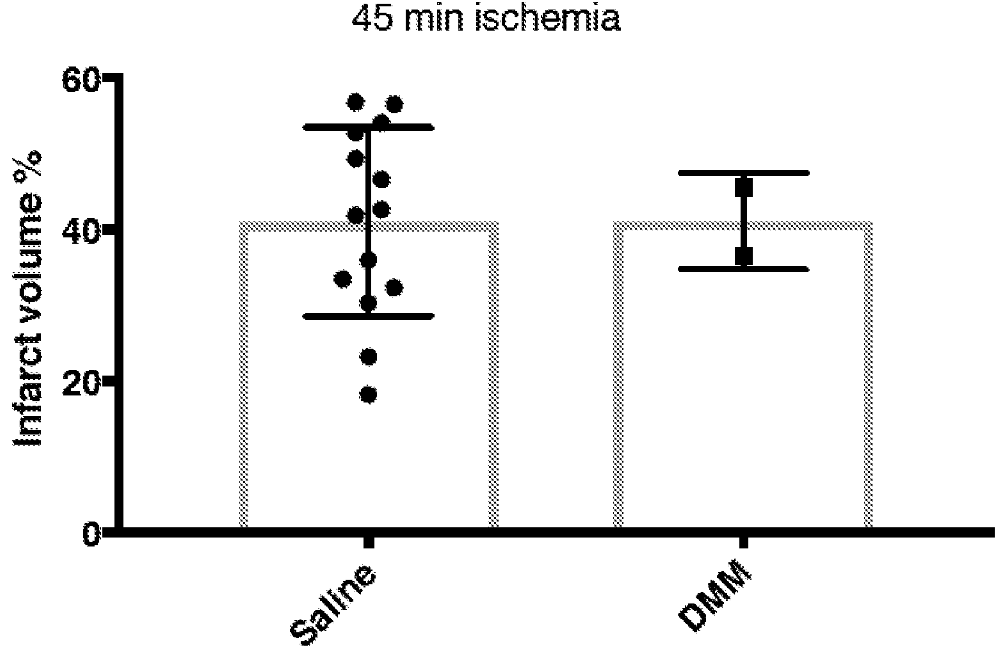
FIG. 3 shows the effect of a comparative compound, dimethyl malonate, on infarct volume following ischaemic stroke vs a saline control.

As set out in WO 2016/001686, dimethyl malonate (DMM) has previously been shown to be protective when administered prior to and throughout ischemia. However, as shown in FIG. 3, it is not effective when given at or immediately prior to stroke reperfusion.

Figure 4:
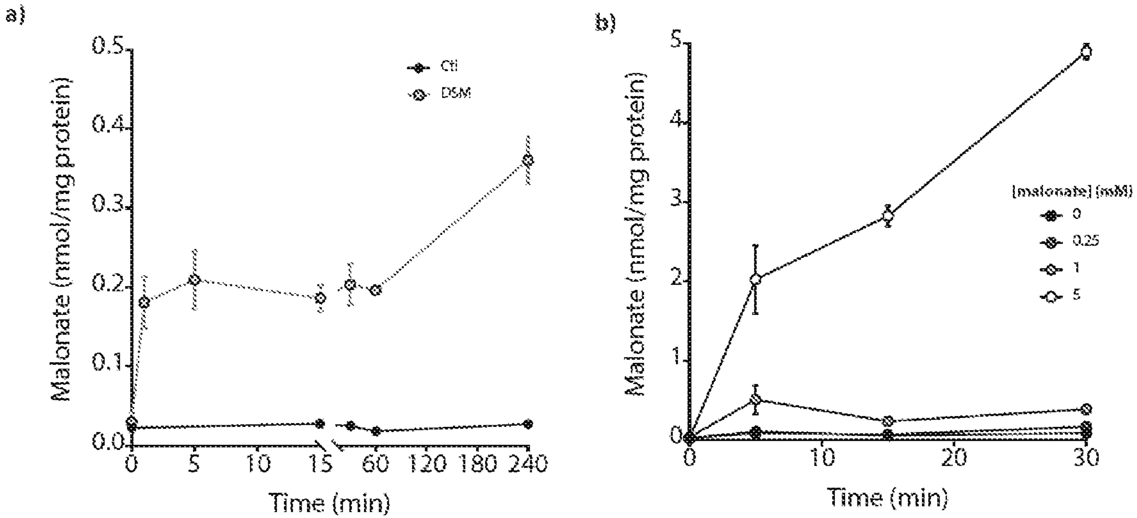
FIG. 4 shows in vitro uptake of a representative compound, disodium malonate, by tissues and cells.

The present invention arises from the surprising finding that malonate salts and related compounds are particularly effective for the treatment and prevention of ischaemic stroke reperfusion injury. This finding is particularly surprising because such salts were previously thought not to be cell permeable in vivo. However as exemplified by FIGS. 4 and 5, such salts are surprisingly able to penetrate into various cells and tissues, including brain tissue.

In particular, the invention relates to salts of formula (I)

Formula (I)

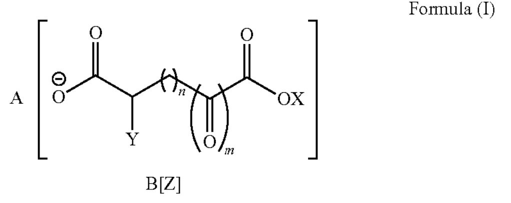

for use in treating or preventing ischaemic stroke reperfusion injury.

In the above formula, X is selected from a negative charge, H, or $C_1$-$C_{12}$ alkyl group. Preferably, X is selected from a negative charge, H or $C_1$-$C_{10}$ alkyl. More preferably, X is selected from a negative charge, H or $C_1$-$C_5$ alkyl.

In the above formula, Y is selected from H, OH or $C_1$-$C_{12}$ alkyl. Preferably, Y is selected from H, OH or $C_1$-$C_{10}$ alkyl. More preferably, Y is selected from H, OH or $C_1$-$C_5$ alkyl.

In the formula above, n is 0 or 1.

In the formula above, m is 0 or 1.

In the formula above, Z is one or more pharmaceutically acceptable cations. Each Z is a pharmaceutically acceptable cation, provided that the net charge of the salt of formula (I) is 0. For example, Z may comprise a cation with a +1 charge, a +2, or a +3 charge. Preferably, Z comprises: a cation selected from $Li^+$, $Na^+$, $K^+$, $Rb^+$, $Cs^+$, $Mg^{2+}$, $Ca^{2+}$, $Sr^{2+}$, $Ba^{2+}$, $Cu^+$, $Cu^{2+}$, $Fe^{2+}$, $Fe^{3+}$, $Pb^{2+}$, $Ni^{2+}$, $Ag^+$, $Sn^{2+}$, $Cr^{3+}$, $Zn^{2+}$, $Al^{3+}$ and/or $NH_4^+$; or a cation selected from $Li^+$, $Na^+$, $K^+$, $Rb^+$, $Cs^+$, $Mg^{2+}$, $Ca^{2+}$, $Sr^{2+}$, $Ba^{2+}$, $Pb^{2+}$, $Ni^{2+}$, $Ag^+$, $Sn^{2+}$, $Cr^{3+}$, $Zn^{2+}$, $Al^{3+}$ and/or $NH_4^+$; or a cation selected from $Li^+$, $Na^+$, $K^+$, $Rb^+$, $Cs^+$, $Mg^{2+}$, $Ca^{2+}$, $Sr^{2+}$, $Ba^{2+}$, $Pb^{2+}$, $Ni^{2+}$, $Sn^{2+}$, $Cr^+$, $Zn^{2+}$ and/or $NH_4^+$; or a cation selected from $Li^+$, $Na^+$, $K^+$, $Mg^{2+}$, $Ca^{2+}$, $Zn^{2+}$ and/or $NH_4^+$.

A and B may independently be any integer (for example, independently 1, 2 or 3), provided that the net charge on the salt of formula (I) is 0. For example, when Z is a +3 cation and the anion is a −2 anion, A is 3 and B is 2, such that the net charge on the salt is 0. In one embodiment, A and B are each independently selected from 1 and 2; for example A is 1 and B is 1 or 2.

Z may be a single ion, for example a $Na^+$ ion, or multiple ions, such as a $Na^+$ and a $K^+$ ion. Thus, salts with multiple cations (such as sodium potassium malonate) are encompassed by formula (I).

In a preferred embodiment, the salt of formula (I) has a value of n of 0, and a value of m of 0. In this case, the salt is a salt of formula (II):

Formula (II)

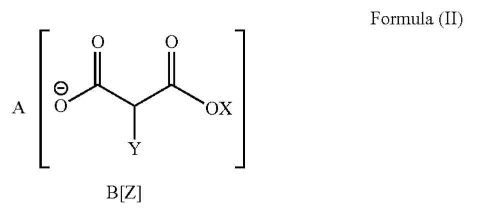

wherein A, B, Z, Y and X are as defined above.

The salt of formula (I) for use in treating or preventing ischaemic stroke reperfusion injury may preferably be a malonate salt. In this case, the salt is of formula (II) and Y is a H atom.

For example, the salt of formula (II) may be disodium malonate, monosodium malonate, dipotassium malonate, monopotassium malonate, dilithium malonate, monolithium malonate, calcium malonate, magnesium malonate, ammonium malonate, aluminium malonate or zinc malonate. Optionally, the salt of formula (II) is disodium malonate.

The use of salts of the present invention, such as malonate salts, nullifies a number of barriers to clinical translation. Salts of the present invention, and in particular malonate salts, can enter mitochondria by endogenous transport mechanisms, thus allowing the compound to reach the target site in a timely manner (as exemplified by FIG. 5). Furthermore, salts of the present invention, and in particular malonate salts, have limited toxicity, well established metabolism and have been used as excipients in pharmaceutical development.

The salt for use in treating or preventing ischaemic stroke reperfusion injury may alternatively be a salt of formula (II), wherein Y is a $C_1$-$C_5$ alkyl, more preferably a butyl group.

The salt of formula (I) may be administered at any point following a suspected ischaemic stroke, for example following observance of one or more stroke symptoms selected from sudden numbness or weakness in the face, arm, or leg, sudden confusion, trouble speaking, or difficulty understanding speech, sudden trouble seeing in one or both eyes, sudden trouble walking, dizziness, loss of balance, or lack of coordination, sudden severe headache, complete paralysis of one side of the body, difficulty swallowing (dysphagia) and loss of consciousness.

As used herein, reperfusion refers to the point at which blood flow into the ischaemic tissue begins following a stroke. Reperfusion may occur naturally (such as following a transient ischaemic attack or mini-stroke), or may be initiated. When reperfusion is initiated, it may by initiated by any method known in the art capable of removing a blockage in blood flow, such as by either mechanical or chemical means. Preferably, reperfusion is initiated by thrombolysis (for example, by administering blood thinning agents or application of lysis agents to the patient), and/or by thrombectomy.

Suitable blood thinning agents may be selected from Coumadin™ (warfarin); Pradaxa™ (dabigatran); Xareito™ (rivaroxaban) and Eliquis™ (apixaban), Fondaparinux, unfractionated heparin, low molecular weight heparins including but not limited to enoxaparin and deltaparin, thrombolytic agents including but not limited to Streptokinase (SK), Urokinase, Lanoteplase, Reteplase, Staphylokinase, Tenecteplase and Alteplase, or antiplatelet drugs such as aspirin, clopidogreal or ticagrelor.

The salt of formula (I) may first be administered to a patient following stroke ischaemia but before reperfusion. Preferably, administration of the salt of formula (I) then continues until reperfusion is established, optionally during reperfusion, optionally until reperfusion is complete.

Administering the salt of formula (I) for a substantial time before initiation or onset of reperfusion ensures that the salt of formula (I) is able to accumulate in concentrations sufficient to minimise the production of ROS on reperfusion, protecting the ischaemic tissue from IR injury. As such, it is preferable to first administer the salt of formula (I) to the patient as soon as possible after onset of stroke symptoms. The salt of formula (I) is thus preferably administered at least on initiation or at the onset of reperfusion, preferably for a time of at least about 5 minutes before initiation or onset of reperfusion, preferably 10 minutes, preferably 15 minutes and preferably 20 minutes or more before initiation or onset of reperfusion.

Alternatively, the salt of formula (I) may first be administered to a patient following initiation or onset of reperfusion. In this case, the salt of formula (I) is preferably first administered to the patient as soon as possible following initiation of reperfusion to minimise IR injury. Following initial administration of the salt of formula (I) to the patient, the administration preferably continues until reperfusion is established, optionally during reperfusion, optionally until reperfusion is complete.

Alternatively, the salt of formula (I) may first be administered to a patient at the point of reperfusion. Preferably, administration of the salt of formula (I) then continues until reperfusion is complete.

The salt of formula (I) may be administered to a patient in combination with a treatment used or intended to remove a blockage in blood flow i.e. a treatment used or intended to initiate reperfusion. This may occur simultaneously, for example when the salt of formula (I) is administered to a patient at the point of reperfusion, or separately; for example the salt of formula (I) is administered following stroke ischaemia but before reperfusion, and the treatment to initiate reperfusion is started subsequently (either during the administration of the salt of formula (I), or after such administration has stopped). Preferably, the salt of formula (I) is administered to a patient in combination with a thrombolysis treatment and/or thrombectomy. Preferably, the thrombolysis treatment is selected from application of blood thinning agents or application of lysis agents to the patient, as defined above.

As set out above, a key advantage of the present invention is that the salts of formula (I) are beneficial for the treatment and prevention of ischaemic stroke reperfusion injury, but are not harmful in the case of haemorrhagic stroke. Thus, a salt of formula (I) can be administered to a patient suspected of having a stroke before diagnosis of the type of stroke. As such, the salts of formula (I) may be used as an emergency medication before diagnosis of type of stroke, which minimises the damage caused upon reperfusion.

Thus, in one embodiment, the present invention relates to a salt of formula (I) as defined herein, for use as an emergency medication following suspected stroke, before diagnosis of the type of stroke. Preferably, the salt is a salt of formula (II), more preferably a malonate salt as defined herein.

In the case of administration as an emergency medication, the salt of formula (I) is preferably administered to a patient suspected of suffering a stroke at any point before diagnosis of the type of stroke, and preferably within about 4 hours of the onset of stroke symptoms, preferably within about 3 hours of the onset of stroke symptoms, preferably within about 2 hours of the onset of stroke symptoms and more preferably within about 1 hour of the onset of stroke symptoms.

The salt of formula (I) may be administered in a setting where it is possible to initiate treatment extremely quickly after stroke symptoms begin, for example in a ward on a hospital. Initiation of administration of a salt of formula (I) can thus begin within about 50 minutes of onset of stroke symptoms, preferably within about 40 minutes of onset of stroke symptoms, preferably within about 30 minutes of onset of stroke symptoms, preferably within about 20 minutes of onset of stroke symptoms and most preferably within about 15 minutes of onset of stroke symptoms.

Regardless of the point at which first administration of the salt of formula (I) occurs, it is preferable to continue administering the salt of formula (I) (e.g. continuously, or at regular intervals) until reperfusion is established, or for ischaemic stroke to be ruled out when the treatment was for a suspected ischaemic stroke. In certain cases, initiation of reperfusion using chemical or mechanical means is not feasible. For example, a patient may have contraindications for thrombolysis, such as an elevated risk of bleeding if thrombolysis is initiated. Alternatively, thrombectomy may not be available at the point of presentation of the patient. In these cases, the salt of formula (I) may be administered continually until reperfusion naturally occurs. As such, the salt of formula (I) may be continually administered for a time of up to 6 hours from time of the initial administration. Preferably, the total time of administration of the salt of formula (I) is greater than about 2 minutes, preferably greater than about 5 minutes, preferably greater than about 10 minutes, and most preferably greater than about 15 minutes. Preferably, the total time of administration of the salt of formula (I) is less than about 5 hours, preferably less than about 4 hours, preferably less than about 3 hours, and most preferably less than about 2 hours.

The salt of formula (I) may be administered as part of a combination therapy to prevent tissue damage. For example, the salt of formula (I) may be administered with other agents or interventions for targeting ischaemic reperfusion injury.

The salt of formula (I) may be administered by any method in the art. Preferably, the salt of formula (I) is administered orally, topically, subcutaneously, parenterally, intramuscularly, intraperitoneally, intraocularly, intranasally, intra-arterially or intravenously. Most preferably, the salt of formula (I) is administered intravenously.

The salt of formula (I) may be administered at a dose in the range of from about 0.1 mg/kg to about 500 mg/kg of body weight. Preferably, the salt of formula (I) is administered at a dose of greater than about 0.2 mg/kg of body weight, preferably greater than about 0.3 mg/kg of body weight, preferably greater than about 0.4 mg/kg of body weight, and preferably greater than about 0.5 mg/kg of body weight. Preferably, the salt of formula (I) is administered at a dose of less than about 450 mg/kg of body weight, preferably less than about 400 mg/kg of body weight, preferably less than about 350 mg/kg of body weight, and preferably less than about 300 mg/kg of body weight.

The salt of formula (I), preferably a salt of formula (II), more preferably a malonate salt, may be formulated into a composition for use in treating or preventing ischaemic stroke reperfusion injury in a subject in need thereof, and/or for use as an emergency medication following suspected stroke, before diagnosis of the type of stroke. The composition comprises the salt of formula (I), preferably a salt of formula (II), more preferably a malonate salt, and one or more pharmaceutically acceptable excipients, carriers or diluents.

Suitable excipients, carriers and diluents can be found in standard pharmaceutical texts. See, for example, Handbook for Pharmaceutical Additives, 3rd Edition (eds. M. Ash and I. Ash), 2007 (Synapse Information Resources, Inc., Endicott, New York, USA) and Remington: The Science and Practice of Pharmacy, 2ist Edition (ed. D. B. Troy) 2006 (Lippincott, Williams and Wilkins, Philadelphia, USA).

Excipients for use in the compositions of the invention include, but are not limited to microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavouring agents, colouring matter or dyes, and, if so desired, emulsifying and/or suspending agents as well, together with such diluents as water, ethanol, propylene glycol, glycerin and various like combinations thereof.

Pharmaceutical carriers include solid diluents or fillers, sterile aqueous media and various non-toxic organic solvents, and the like.

Pharmaceutically acceptable carriers include gums, starches, sugars, cellulosic materials, and mixtures thereof. The compound can be administered to a subject by, for example, subcutaneous implantation of a pellet. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

Further, as used herein "pharmaceutically acceptable carriers" are well known to those skilled in the art and include, but are not limited to, 0.01-0.1 M and preferably 0.05 M phosphate buffer or 0.9% saline. Additionally, such pharmaceutically acceptable carriers maybe aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Pharmaceutically acceptable parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Pharmaceutically acceptable carriers for controlled or sustained release compositions administrable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Pharmaceutically acceptable carriers include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski and Davis, *Soluble Polymer-Enzyme Adducts, Enzymes as Drugs*, Hocenberg and Roberts, eds., Wiley-Interscience, New York, N.Y., (1981), pp 367-383). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The present invention also relates to a method of treating or preventing ischaemic stroke reperfusion injury in a subject, the method comprising administering a salt of formula (I) as defined herein, or a composition as defined herein to the subject. The present invention also relates to an emergency method of treatment of suspected stroke before diagnosis of the type of stroke in a subject, the method comprising administering a salt of formula (I) as defined herein, or a composition as defined herein to the subject. Preferably, the salt is a salt of formula (II), more preferably a malonate salt as defined herein. Preferably, the method comprises administration of said salt to the subject as further defined herein.

The present invention also relates to the use of a salt of formula (I) as defined herein, or a composition as defined herein for the manufacture of a medicament for treating or preventing ischaemic stroke reperfusion injury. The present invention also relates to the use of a salt of formula (I) as defined herein, or a composition as defined herein for the manufacture of a medicament for use as an emergency medication following suspected stroke, before diagnosis of the type of stroke. Preferably, the salt is a salt of formula (II), more preferably a malonate salt as defined herein. Preferably, said salt is for manufacture of a medicament for preventing ischaemic stroke reperfusion injury as further defined herein.

As used herein, the term "$C_1$-$C_n$ alkyl" refers to straight chain and branched saturated hydrocarbon groups generally having from 1 to n carbon atoms. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, and the like.

As used herein, the terms "drug", "drug substance", "active pharmaceutical ingredient", and the like, refer to a compound that may be used for treating a subject in need of treatment.

As used herein, the term "excipient" refers to any substance that may influence the bioavailability of a drug, but is otherwise pharmacologically inactive.

As used herein, the term "pharmaceutically acceptable" refers to species which are within the scope of sound medical judgment suitable for use in contact with the tissues of subjects without undue toxicity, irritation, allergic response, and the like, commensurate with a reasonable benefit-to-risk ratio, and effective for their intended use.

As used herein, the term "pharmaceutical composition" refers to the combination of one or more drug substances and one or more excipients.

As used herein, the term "subject" as used herein refers to a human or non-human mammal.

Examples of non-human mammals include livestock animals such as sheep, horses, cows, pigs, goats, rabbits and deer; and companion animals such as cats, dogs, rodents, and horses.

As used herein, the term "body" as used herein refers to the body of a subject as defined above.

As used herein, the term "therapeutically effective amount" of a drug refers to the quantity of the drug or composition that is effective in treating a subject and thus producing the desired therapeutic, ameliorative, inhibitory or preventative effect. The therapeutically effective amount may depend on the weight and age of the subject and the route of administration, among other things.

As used herein, the term "treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

As used herein, the term "treatment" refers to the act of "treating", as defined above.

As used herein, the term "preventing" refers to a reduction of the risk of acquiring a given disease or disorder, or a reduction in the severity of symptoms of the given disease or disorder if the disease or disorder is acquired after the preventative measure. Hence, "preventing" refers to the prophylactic treatment of a subject in need thereof. The prophylactic treatment can be accomplished by administering an appropriate dose of a therapeutic agent to a subject having a predisposition to a disorder, or at risk of developing a disorder, even though symptoms of the disorder are absent or minimal, thereby substantially averting onset of the disorder, or substantially reducing the severity of symptoms of the disorder if it is acquired after the preventive measure.

As used herein, the term "succinate dehydrogenase inhibitor" or "SDHi" refers to a species that inhibit the action of succinate dehydrogenase.

As used herein, the term "thrombolysis" refers to removal of a blockage to blood flow, for example a blood clot, using chemical means, for example through the use of thrombolytic agents.

As used herein, the term "thrombectomy" refers to removal of a blockage to blood flow, for example a blood clot, using mechanical means.

As used herein the term "comprising" means "consisting at least in part of". When interpreting each statement in this specification that includes the term "comprising", features other than that or those prefaced by the term may also be present. Related terms such as "comprise" and "comprises" are to be interpreted in the same manner.

EXAMPLES

Example 1—Transient Middle Cerebral Artery Occlusion (MCAO) Model

Male C57Bl6J mice, 6-8 weeks old, were anesthetized with 3% isoflurane and anaesthesia was maintained on 1.5-2% isoflurane. A Doppler flowmetry probe (Perimed, Sweden) was attached to the skull to continuously monitor the cerebral blood flow. Left common carotid artery (CCA) and left external carotid artery were exposed and permanently ligated. Left internal common carotid artery was clamped temporarily. Next, an incision was made on CCA and a filament with a silicon tip (0.22 mm in diameter, 2-3 mm in length, Doccol, USA) was inserted and guided forward into internal carotid artery until it reached middle cerebral artery (MCA). The occlusion of MCA was confirmed by seeing at least 70% drop in cerebral blood flow. After 45 minutes ischemia, the filament was retracted to allow reperfusion for 2 hours. The reperfusion was confirmed when the cerebral blood flow reached to 80% of that of baseline.

Either disodium malonate (DSM) or vehicle control was given i.v. for 20 min starting just prior to reperfusion.

At the end of reperfusion, mice were sacrificed by cervical dislocation; brain was collected and sliced at 2 mm thicknesses and stained with 2% triphenyltetrazolium chloride in saline at 37 C for 10-15 min. Then, brain slices were fixed with 4% paraformaldehyde overnight and imaged using a scanner. The healthy tissue area (red-stained) in both hemispheres was measured using ImageJ. The infarct volume % was calculated by first calculating the volume of healthy tissue in each hemisphere (Σ area of each slice×thickness of slice), then by the formula: ((volume of healthy tissue in uninjured hemisphere −volume of healthy tissue in injured hemisphere) ÷volume of healthy tissue in uninjured hemisphere)×100.

Figure 1:
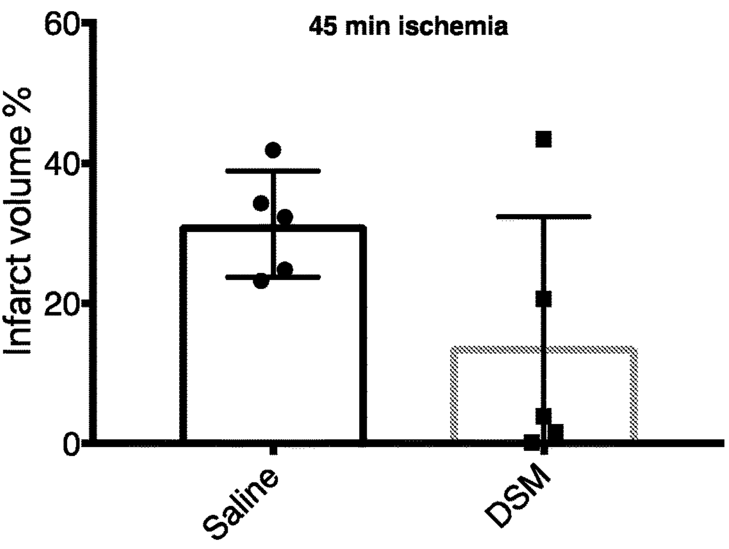
FIG. 1 shows the effect of a representative compound, disodium malonate, on infarct volume following ischaemic stroke vs a saline control.

As shown in FIG. 1, necrotic brain infarct volume was decreased when DSM was given for 20 minutes starting just prior to reperfusion.

Figure 2:
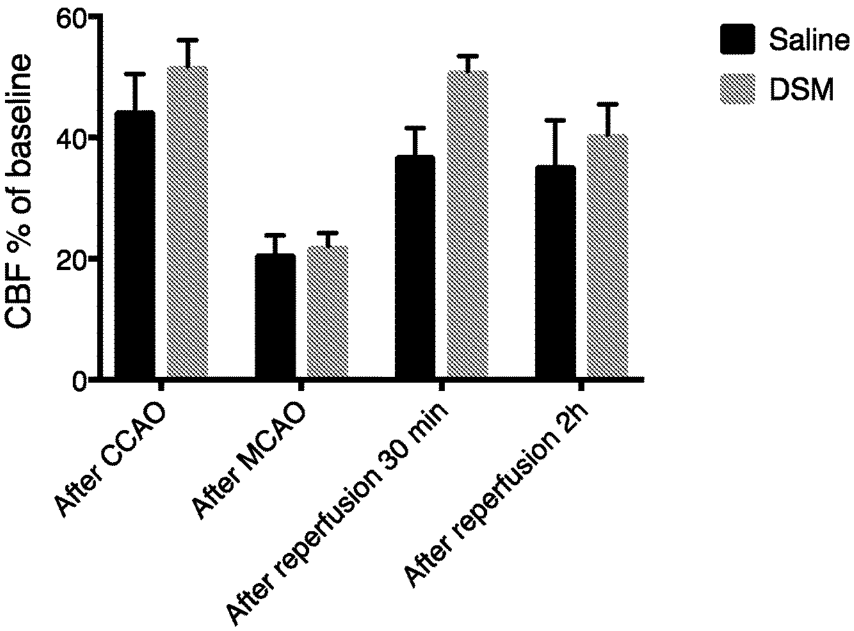
FIG. 2 shows the effect of a representative compound, disodium malonate, on cerebral blood flow (CBF) at various points during ischaemic stroke and reperfusion, vs a saline control.

As shown in FIG. 2, cerebral blood flow was significantly reduced during transient middle cerebral artery occlusion (MCAO). Administering DSM for 20 minutes starting immediately prior to reperfusion did not significantly alter the blood flow during the procedure, showing that DSM targets reperfusion injury rather than cerebral blood flow.

Comparative Example 1

The method of Example 1 was performed, except that dimethyl malonate (DMM) was administered instead of DSM. As shown in FIG. 3, there was no significant difference in necrotic brain infarct volume when DMM was given for 20 minutes starting just prior to reperfusion.

Example 2—Malonate Uptake in Vitro

We first explored whether malonate could be taken up by cells in culture. C2Cl2 mouse myoblast cells were plated at 300,000 cells/well and adhered overnight. The next day, cells were treated with either DSM (a—0.25 mM; b—0.25, 1 or 5 mM) or untreated for 0 to 240 min before cooling plates on ice and rapidly washing 4 times with ice-cold PBS and placed on dry ice. Cells were extracted for mass spectrometry with 500 μl extraction buffer (50% methanol, 30% acetonitrile and 20% water) with 1 nmol $^{13}C$-malonate internal standard centrifuged to remove insoluble debris.

This showed that there was rapid malonate uptake into cells, reaching intracellular levels of ~0.2-0.4 nmol/mg protein when incubated with 250 μM disodium malonate (FIG. 4*a*). Malonate uptake was both dose and time-dependent (FIG. 4*b*), with 5 mM DSM achieving high levels of intracellular malonate (~2 nmol/mg protein) after 5 min. Allowing for a cell volume of 260 mg protein/ml, the malonate concentration within the cell after 5 min incubated with 250 μM or 5 mM malonate the intracellular concentrations are about 50 and 500 respectively.

Example 3—Malonate Uptake in Vivo

To see if this uptake also occurred in vivo, we injected disodium malonate into a normoxic mouse by a bolus in the tail vein and measured the malonate levels in tissues 5 min later. C57/BL6 mice were tail vein injected with DSM (160 mg/kg) before cervical dislocation 5 min after the injection, tissues harvested and clamp frozen in liquid nitrogen. For tissue analysis, tissues were weighed and extracted in 25 μl/mg extraction buffer containing internal standard and homogenised in a Precellys 24 homogeniser. Homogenates were centrifuged to remove insoluble debris. Extracts were analysed by LC-MS/MS and the levels of malonate assessed by interpolation of a malonate standard curve.

Figure 5:
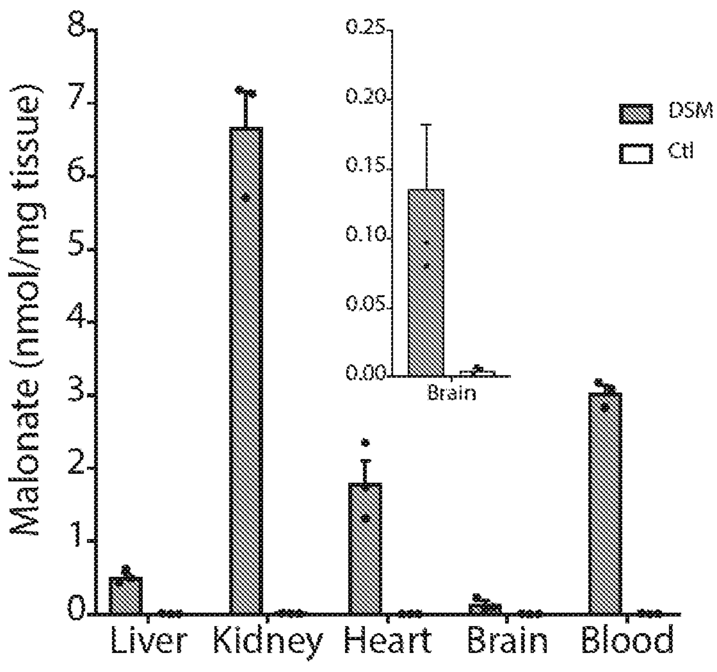
FIG. 5 shows in vivo uptake of a representative compound, disodium malonate, by mouse tissues.
Figure 6:
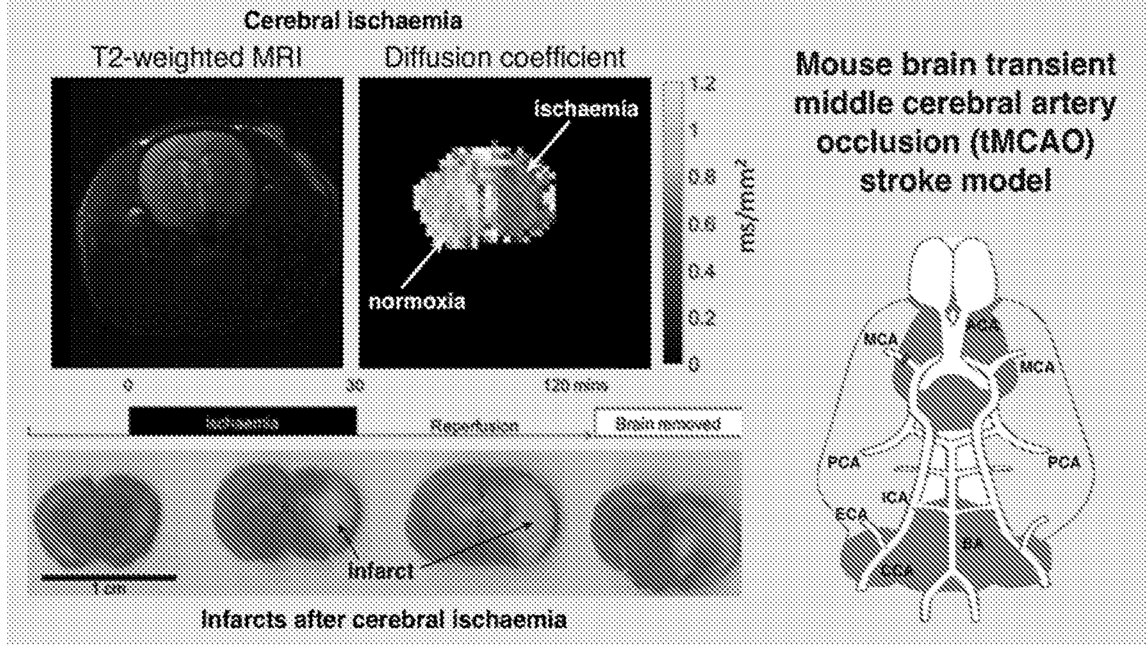
FIG. 6 shows a mouse model of acute ischaemic stroke in vivo.
Figure 7:
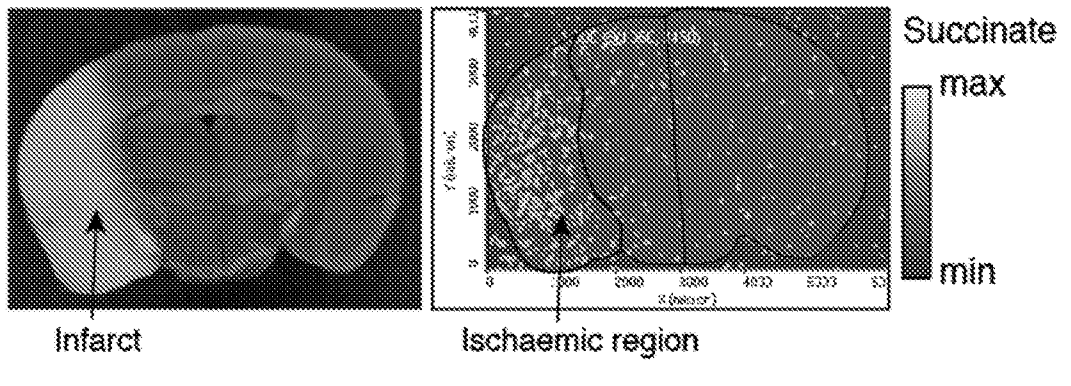
FIG. 7 shows a MALDI image of succinate levels in acute middle cerebral artery (MCA) occlusion.
Figure 8:
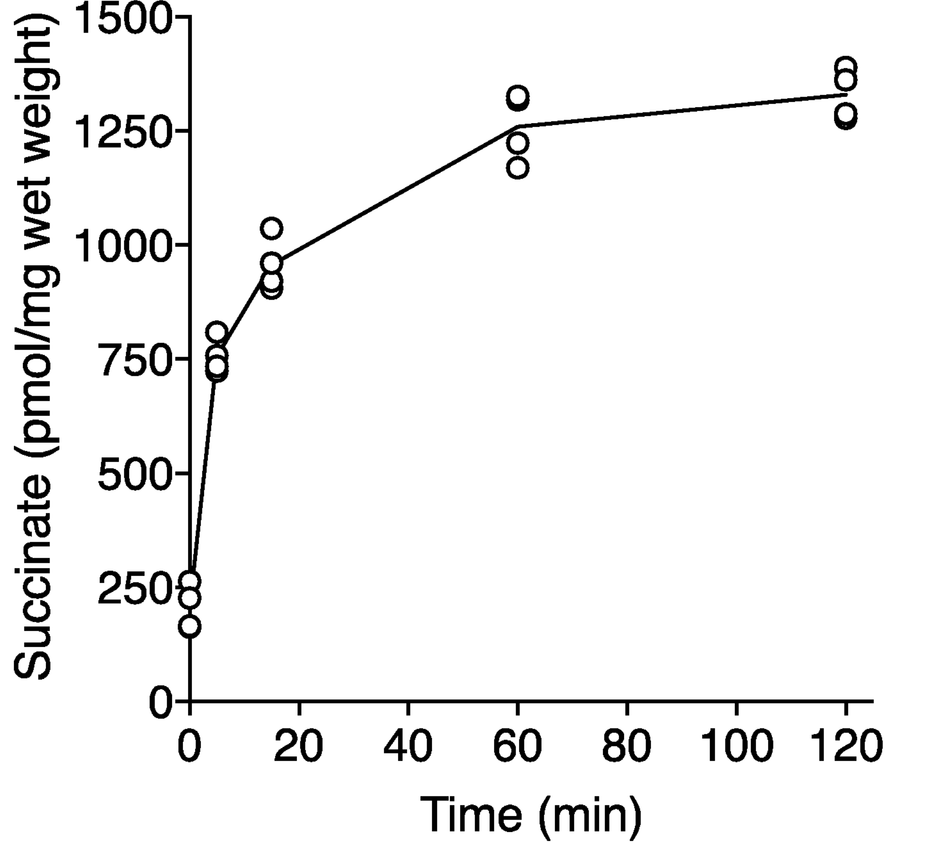
FIG. 8 shows accumulation of succinate during stroke in mouse brains.
Figure 9:
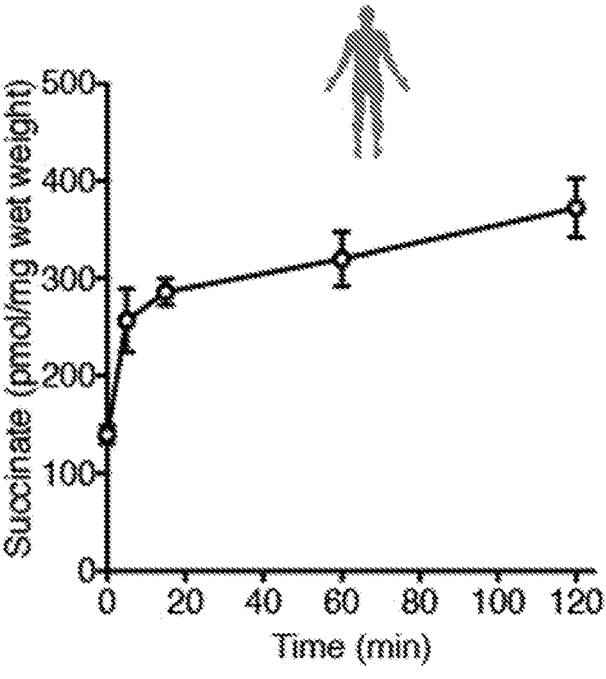
FIG. 9 shows accumulation of succinate during stroke in human brains.
Figure 10:
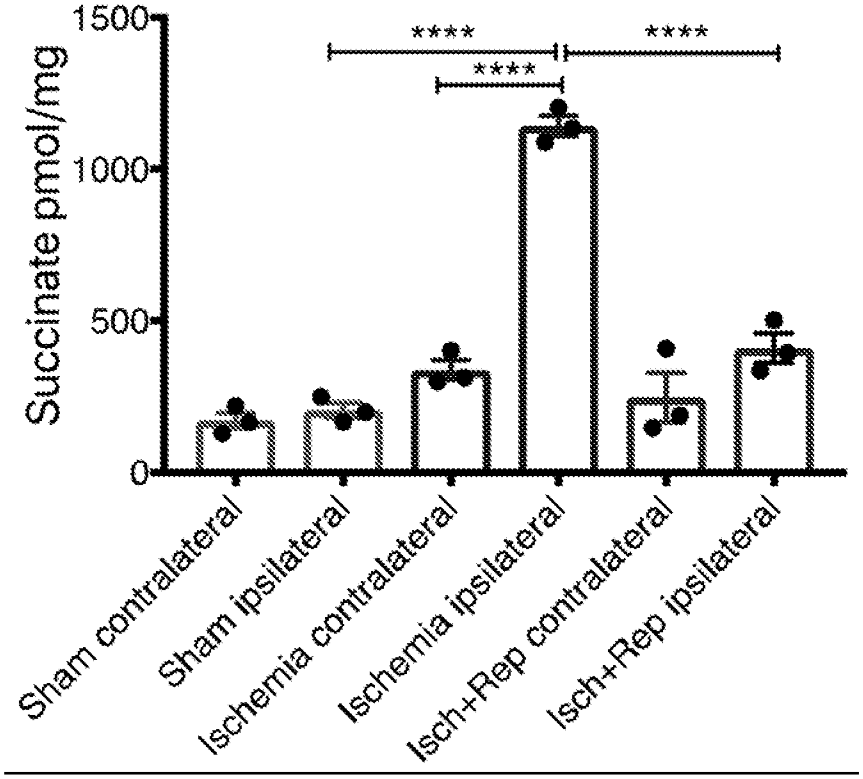
FIG. 10 shows ischaemic succinate levels in brain tissue from a mouse stroke model.
Figure 11:
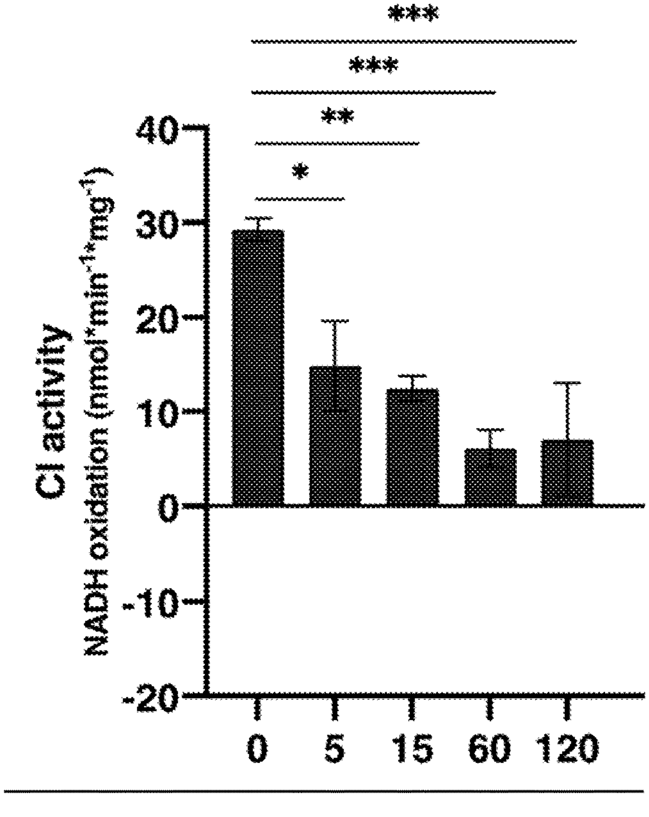
FIG. 11 shows Complex I activity in brain tissue from a mouse stroke model.
Figure 12:
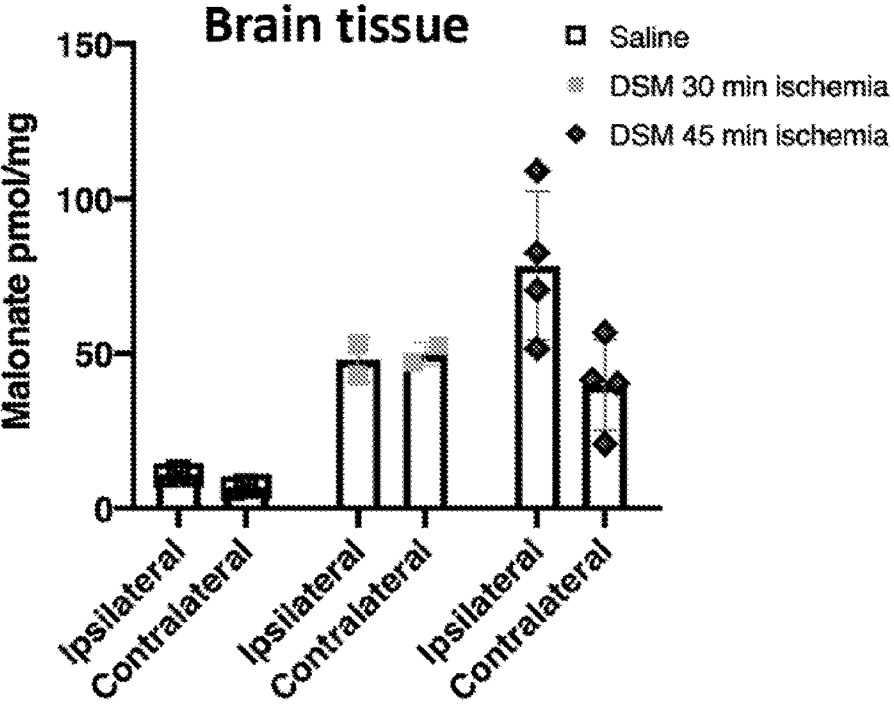
FIG. 12 shows levels of malonate in mouse brain tissue following administration of disodium malonate from 5 minutes before until 5 minutes after reperfusion.
Figure 13:
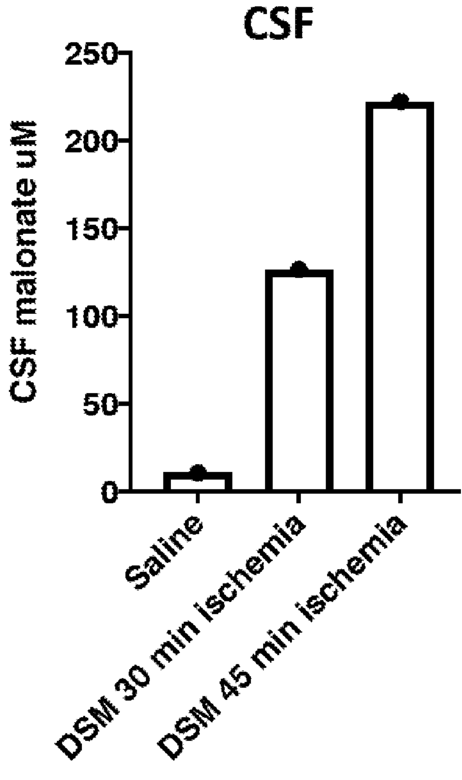
FIG. 13 shows levels of malonate in mouse cerebrospinal fluid (CSF) following administration of disodium malonate from 5 minutes before until 5 minutes after reperfusion.
Figure 14:
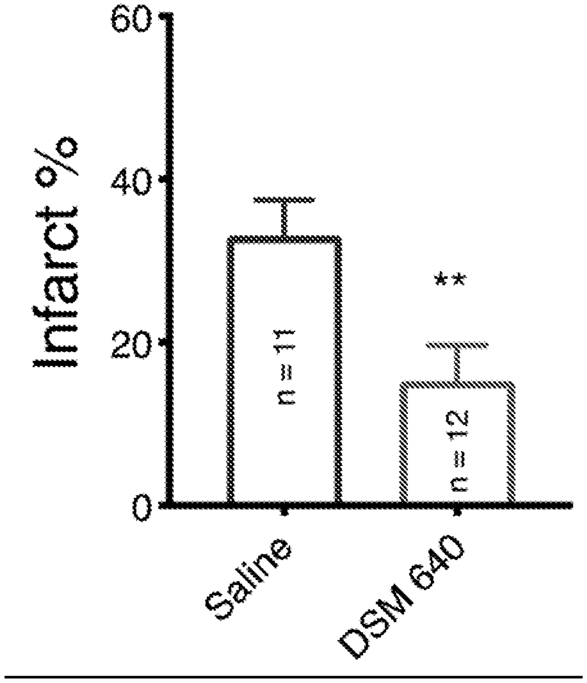
FIG. 14 shows the effect of disodium malonate on infarct size in an acute ischaemic mouse stroke model.

This showed tissue levels of malonate to be particularly high in the kidney with significant amounts in the heart and liver and also uptake in the brain (FIG. 5). This was consistent with tissue uptake of malonate.

Example 4

Animals

Male C57Bl6J mice were purchased from Charles River Laboratories and housed in a room on a 12 h light/dark cycle with ad libitum access to food and water. Mice were acclimatized for a week before being used in the experiments. All experimental procedures were carried out in accordance to the UK Animals Act 1986 and the University of Cambridge Animal Welfare policy and were approved by Home Office (Project License 70/8238 and 70/08840).

Human and Mouse Brain Warm Ischemia

Mice, 8-10 weeks old were sacrificed by cervical dislocation and the brain were clamp-frozen immediately or after 5, 15, 60 or 120 minutes of warm ischemia at 37° C. Human brain biopsies were retrieved from patients undergoing surgeries for brain tumours in collaboration with Dr Richard Mair, Neurosurgery Cambridge. The biopsies (20-80 mg) were rapidly cut into 3 to 5 pieces depending on the tissue size. One piece was frozen immediately (time from dissection to freezing: 30 s to 2 min) and the other pieces were incubated at 37° C. for indicated time periods (5 min to 120 min) of warm ischemia and then clamp-frozen.

Metabolite Extraction

Approximately 20 mg of mouse brain tissue and 5-20 mg of human brain tissue was weighed on dry ice and placed in pre-chilled Precellys tube (CK28-R, Bertin Instruments, France). Next, 25 μl/mg dry-ice cold extraction buffer (50% [v/v] methanol, 30% [v/v] acetonitrile and 20% [v/v] $H_2O$), supplemented with 1 nmol of [$^{13}C_4$]-succinate (Sigma Aldrich, UK) was added to the tubes and the tissue was homogenized using a Precellys 24 tissue homogeniser (6,500 rpm, 15 s; Bertin Instruments, France). The homogenizing program was run again after 5 min incubation on dry ice. Samples were then centrifuged at 17000 rpm at 4° C. and the supernatant was collected and incubated in −20° C. freezer for 1 h. The centrifuging step was repeated two times and the supernatant was transferred to pre-chilled MS vials and were stored at −80° C. until analysis for succinate by liquid chromatography-tandem mass spectrometry (LC-MS/MS).

LC-MS/MS for Quantification of Succinate

LC-MS/MS analysis of succinate was performed using an LCMS-8060 mass spectrometer (Shimadzu, UK) with a Nexera X2 UHPLC system (Shimadzu, UK). Samples were stored in a refrigerated autosampler (4° C.) upon injection of 5 μl into a 15 μl flowthrough needle. Separation was achieved using a SeQuant® ZIC®-HILIC column (3.5 μm, 100 Å, 150×2.1 mm, 30° C. column temperature; Merck-Millipore, UK) with a ZIC®-HILIC guard column (200 Å, 1×5 mm). A flow rate of 200 μl/min was used with mobile phases of A) 10 mM ammonium bicarbonate and B) 100% acetonitrile. A gradient of 0-0.1 min, 80% MS buffer B; 0.1-4 min, 80%-20% B; 4-10 min, 20% B, 10-11 min, 20%-80% B; 11-15 min, 80% B was used. The mass spectrometer was operated in negative ion mode with multiple reaction monitoring (MRM) and spectra were acquired using Lab solutions software (Shimadzu, UK), with compound quantities calculated from relevant standard curves in MS extraction buffer and comparing against [$^{13}C_4$]-succinate internal standard.

Measurement of Mitochondrial Complex I Activity

Frozen mouse brain weighing 7-10 mg were lysed in ice-cold 400 ml of 50 mM $KH_2PO_4$ (KPi buffer) using Precellys CK14 tubes and a Precellys tissue homogenizer (Bertin Instruments) at 6500 rpm, one 15 s cycle. The homogenates were rapidly aliquoted and frozen in dry-icecold tubes and stored in −80° C. until further processing. The protein concentration was measured following standard BCA assay. New aliquots of samples were diluted in KPi buffer containing 0.05% dodecyl maltoside (DDM) to obtain 5 μg total protein amount in 100 μl of buffer for complex I activity assay. In a 96-well plate, 40 μl of the assay buffer (200 μM KCN and 0.3 μM antimycin A in KPi buffer) were added in each well, followed by adding 5 μl of either ethanol+100 μM decylubiquinone or 5 μl of ethanol+0.5 μM of rotenone. The assay was started by adding 50 μl of freshly-prepared 0.8 mM NADH. The NADH oxidation was measured in a plate reader by monitoring absorbance at λ=340 and 380 (8-10 s intervals) for 30 min. The samples were run as duplicates. The maximum linear rate of NADH oxidation was calculated by subtracting the absorbance at 340-380 nm and the background rate was removed by subtracting the rate in samples with rotenone. The NADH concentration was determined using the Beer-Lambert law and the extinction coefficient ε340-380=4.81 $mM^{-1}$ $cm^{-1}$.

Middle Cerebral Artery Occlusion (MCAO) Non-Recovery Model of Stroke

Mice, 8-12 weeks old and weighing 22-30 grams were anesthetized by isoflurane (3% induction, 1.5-2% maintenance) delivered in 100% oxygen. A Doppler (PeriFlux System 5000, Perimed, Sweden) flowmetry probe was attached to the skull on the ipsilateral side to monitor and record the blood circulation at MCA territory. Next, left common carotid artery (CCA) and external carotid artery were exposed and permanently ligated. After temporary occluding the left internal carotid artery by a clamp, an incision was made on CCA, a 6-0 suture with a silicone-coated tip (602223PK10RE, Doccol, USA) was inserted, clamp was removed and the suture was inserted forward until a drop in blood flow was observed on Doppler confirming the MCAO. The ischemia duration was either 30 min or 45 min and then the suture was removed allowing the reperfusion. For metabolite analysis mice were sacrificed at indicated time points after ischemia or reperfusion, sacrificed by cervical dislocation and ipsilateral and contralateral regions of the brain were rapidly dissected and clamp-frozen. For infarct measurement, the mice were kept under anaesthesia for a 2 h period of reperfusion and then sacrificed by cervical dislocation. The brain was dissected out and sliced freshly for staining and infarct size measurement. Mice were excluded from the study if the drop in blood flow after MCAO was higher than 30% of that of baseline or for surgical reasons such as excessive bleeding. No exclusion was performed after endpoint measurements.

Matrix-Assisted Laser Desorption/Ionization (MALDI) Imaging of Succinate

Mice underwent MCAO surgery (30 min ischemia ±5 min reperfusion) as above and the brain was immediately dissected out and frozen in liquid nitrogen-cold isopentane. Coronal sections were cut at 20 μm thickness and mounted on a slide (Superfrost Plus, Thermo Scientific, UK) and were rapidly dried on a heat pad at 60° C. and stored in −80° C. until analysis. Two sections per brain at the level of striatum (MCA territory) was used for MALDI. The matrix solution (1,5-diaminonaphtalene in 80:20 MeOH:H2O v/v, 10 mg/ml) was sprayed on the sections (20 layers) using a nebulized sprayer (Suncollect MALDI spotter; KR Analytical, Cheshire, UK). Imaging was performed using a MALDI LTQ Orbitrap XL (Thermo Fisher Scientific, Hemel Hempstead, UK). Spectra were acquired in negative ion mode for mitochondrial metabolites. The identity of metabolites was obtained by comparing observed to theoretical m/z values. Succinate was detected at 117.0166 m/z. Images were reconstructed using ImageQuest (Thermofisher).

Cerebrospinal Fluid (CSF) Collection after MCAO

Mice underwent non-recovery MCAO surgery and were sacrificed by an overdose of sodium pentobarbital at indicated time points. Next, the mice were perfused with ice-cold PBS via left ventricle for 2.5 minute at a rate of 2 ml/min. CSF was collected from cisterna magna using a glass capillary.

Disodium Malonate Treatment

The non-recovery surgery mice were treated intravenously (i.v.) with disodium malonate (DSM) or the vehicle (phosphate buffered saline, PBS) 10 minutes before reperfusion infused i.v. at a rate of 5 μl/min. Total injected volume was 100 μl. No randomization was performed in non-recovery surgeries, but the investigator measuring the infarct was blinded to the treatment groups. For the recovery surgeries, an investigator randomly ID-numbered Eppendorf tubes containing DSM or PBS. The surgeon randomly chose a tube for treatment. Therefore, the surgeon and investigators analysing the behaviour and infarct volume were blinded to the treatments throughout the experiments and measurements. Mice weighing 22-28 (24.7±1.4; Mean±SD) grams received 4 mg DSM in 100 μl PBS (162.2±9.1 mg/kg; Mean±SD) or the PBS only, infused i.v. at a rate of 10 μl/min starting 5 minutes before reperfusion.

Infarct Volume Measurement after Non-Recovery MCAO

Figure 15:
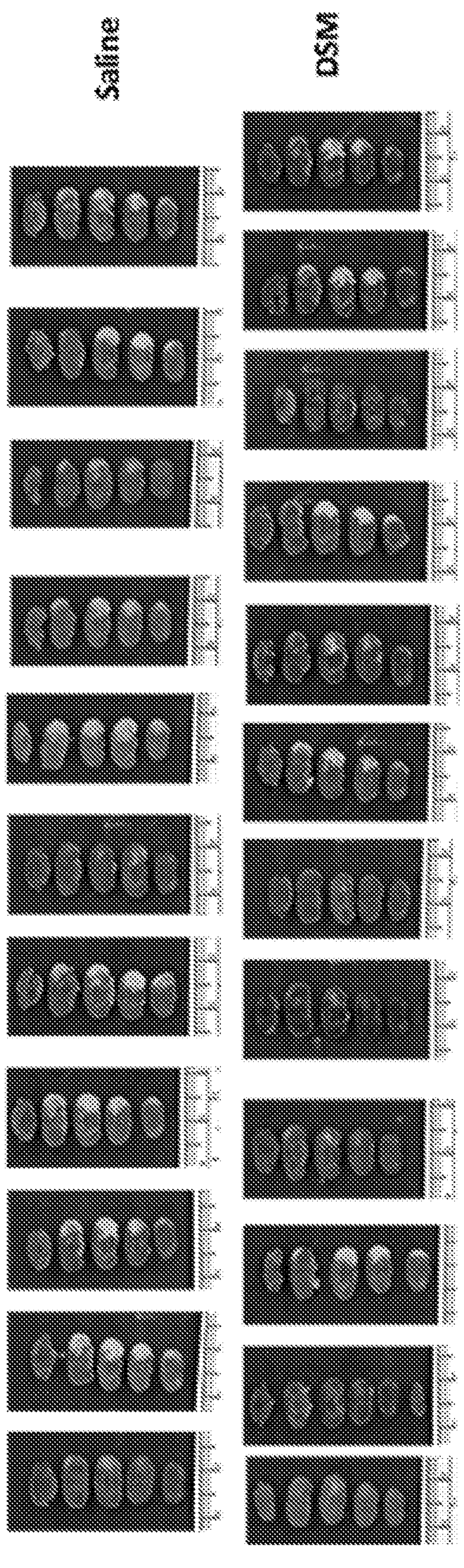
FIG. 15 shows the brains used to generate data presented in FIG. 14. Pale brain regions represent infarct regions.

Brains from the mice that underwent non-recovery surgery were immediately sliced at 2 mm thickness and stained in 2% triphenyltetrazolium chloride (TTC) at 37° C. for 10 min to identify infarct area (shown in FIG. 15). The slices were fixed in 4% paraformaldehyde overnight and were imaged using a scanner. The healthy area (stained red) was measured in two hemispheres. The infarct area was calculated as (Contralateral healthy area−ipsilateral healthy area). The infarct volume was calculated as sum of (infarct area× slice thickness) and was presented as percentage of the healthy hemisphere volume.

Statistics

For infarct size comparing two groups, non-parametric Mann-Whitney test was performed. For multiple group comparisons (blood flow and succinate quantity) one-way or two-way ANOVA was carried out with Tukey's or Sidak's post-hoc tests. All statistical analysis was carried out using Graphpad Prism version 7.0e.

Example 5—Metabolites in Venous Blood of Stroke Patients

Figure 16:
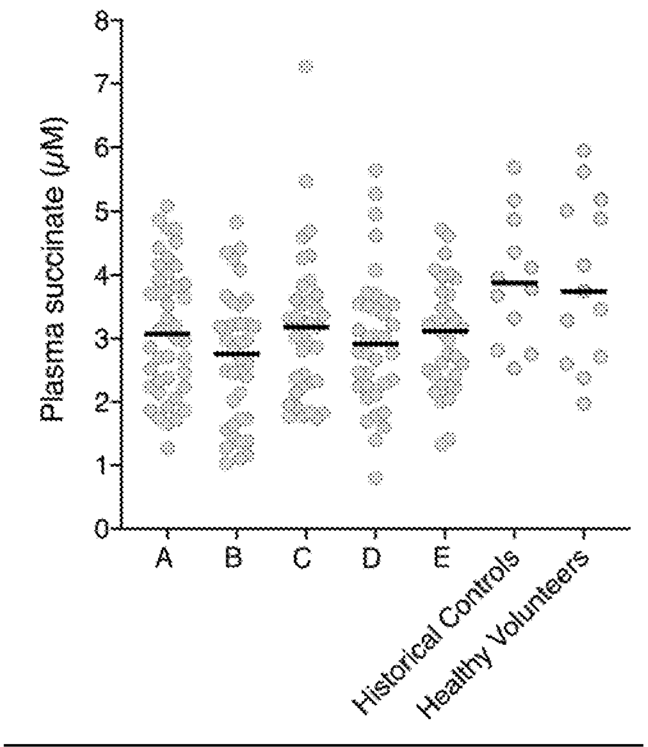
FIG. 16 shows plasma succinate levels in venous blood from patients undergoing thrombolysis due to an acute ischaemic stroke.

Venous blood was taken from patients before and following thrombolysis due to an acute ischaemic stroke at 5 time points: A—before initiation of thrombolysis; B—5 min, C—15 min, D—30 min, and E—60 min after the start of the thrombolysis. The blood samples were analysed for plasma succinate levels. Healthy controls were age and sex matched. Results are shown in FIG. 16. No increase in succinate was evident in venous blood from patients undergoing thrombolysis.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the claims set out below.

The invention claimed is:

1. A method of treating or preventing ischaemic stroke reperfusion injury in a subject, the method comprising administering a malonate salt of formula (II) to the subject:

Formula (II)

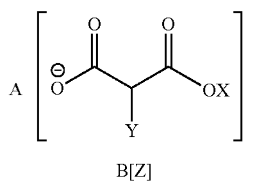

wherein X is selected from a negative charge, H, or $C_1$-$C_{12}$ alkyl;

wherein Y is H;

wherein Z is one or more pharmaceutically acceptable cations; and wherein A and B are independently any integer, such that the net charge of the salt is 0.

2. The method according to claim 1, wherein X is selected from a negative charge, H, or $C_1$-$C_5$ alkyl.

3. The method according to claim 1, wherein X is a negative charge.

4. The method according to claim 1, wherein each Z is independently selected from $Li^+$, $Na^+$, $K^+$, $Rb^+$, $Cs^+$, $Mg^{2+}$, $Ca^{2+}$, $Sr^{2+}$, $Ba^{2+}$, $Cu^+$, $Cu^{2+}$, $Fe^{2+}$, $Fe^{3+}$, $Pb^{2+}$, $Ni^{2+}$, $Ag^+$, $Sn^{2+}$, $Cr^{3+}$, $Zn^{2+}$, $Al^{3+}$ and $NH_4^+$.

5. The method according to claim 1, wherein the salt is disodium malonate, monosodium malonate, dipotassium malonate, monopotassium malonate, dilithium malonate, monolithium malonate, calcium malonate, magnesium malonate, ammonium malonate, aluminium malonate or zinc malonate.

6. The method according to claim 1, the method comprising administering the salt orally, topically, subcutaneously, parenterally, intramuscularly, intraperitoneally, intraocularly, intranasally, intra-arterially or intravenously.

7. The method according to claim 1, the method comprising administering the salt intravenously.

8. The method according to claim 1, the method comprising beginning administration of the salt following stroke ischaemia and before reperfusion.

9. The method according to claim 1, the method comprising administering the salt during reperfusion.

10. The method according to claim 1, the method comprising administering the salt as an emergency medication before diagnosis of type of stroke.

11. The method according to claim 1, the method comprising administering the salt within one hour of the onset of stroke symptoms.

12. The method according to claim 1, the method comprising administering the salt for a total time in the range of from about 10 minutes to about 2 hours.

13. The method according to claim 1, the method comprising administering the salt in combination with a treatment used or intended to remove a blockage in blood flow.

14. The method according to claim 13, wherein the treatment used or intended to remove a blockage in blood flow is selected from thrombolysis by application of blood thinning agents or application of lysis agents, and thrombectomy.

15. The method according to claim 1, the method comprising administering the salt in a dosage in the range of from about 0.1 mg/kg to about 500 mg/kg of body weight.

16. The method according to claim 1, the method comprising administering the salt as a combination therapy to prevent tissue damage.

17. A method of treating or preventing ischaemic stroke reperfusion injury in a subject, the method comprising administering a composition to the subject, the composition comprising a salt of formula (II):

Formula (II)

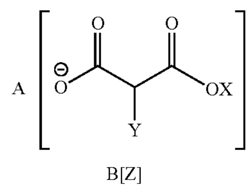

in combination with one or more pharmaceutically acceptable excipients, carriers or diluents;

wherein X is selected from a negative charge, H, or $C_1$-$C_{12}$ alkyl;

wherein Y is H;

wherein Z is one or more pharmaceutically acceptable cations; and wherein A and B are independently any integer, such that the net charge of the salt is 0.

18. The method according to claim 1, the method comprising beginning administration of the salt following stroke ischaemia and before reperfusion, wherein the salt is administered for a time of at least 10 minutes before the onset of reperfusion.

19. The method according to claim 1, the method comprising administering the salt in a dosage in the range of from about 0.5 mg/kg to about 100 mg/kg of body weight.

* * * * *